US010627545B2

(12) United States Patent
Stettler et al.

(10) Patent No.: US 10,627,545 B2
(45) Date of Patent: *Apr. 21, 2020

(54) DISTRIBUTED SYSTEMS FOR STORMWATER MONITORING AND REPORTING

(71) Applicant: STORMSENSOR INC, Seattle, WA (US)

(72) Inventors: Anya Rose Stettler, Kennmore, WA (US); Robert Bruce Darling, Lake Forest Park, WA (US); William Irl Gibbs, IV, Seattle, WA (US)

(73) Assignee: STORMSENSOR INC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/383,529

(22) Filed: Apr. 12, 2019

(65) Prior Publication Data

US 2019/0235130 A1    Aug. 1, 2019

Related U.S. Application Data

(63) Continuation of application No. 15/480,084, filed on Apr. 5, 2017, now Pat. No. 10,302,817.

(Continued)

(51) Int. Cl.
*G01F 23/26* (2006.01)
*G01W 1/14* (2006.01)
(Continued)

(52) U.S. Cl.
CPC ............... *G01W 1/14* (2013.01); *E03F 1/00* (2013.01); *G01F 1/002* (2013.01); *G01F 1/663* (2013.01); *G01F 15/063* (2013.01); *G01F 15/066* (2013.01); *G01K 13/02* (2013.01); *G01K 2013/026* (2013.01); *G01N 33/18* (2013.01)

(58) Field of Classification Search
CPC ........ G01W 1/14; G01C 13/002; G01F 1/663; G01K 13/02; G01K 2013/026; G01N 33/18
See application file for complete search history.

(56) References Cited

U.S. PATENT DOCUMENTS 4,958,514 A    9/1990   Takami et al.
5,155,472 A   10/1992   Dam
(Continued)

*Primary Examiner* — Munear T Akki
(74) *Attorney, Agent, or Firm* — Shook Hardy & Bacon, L.L.P.

(57) ABSTRACT

Distributed systems and methods for the automatic monitoring and reporting of data relating to the chemistry and flow of stormwater (i.e. stormwater data) are presented. Multiple fluid sensor devices are exposed to stormwater via positioning the sensor devices in locations of interest. The sensor devices are arranged in self-healing mesh networks. The sensor devices are enabled to acquire stormwater data indicating various fluid properties that are desired to be monitored. A sensor device is further enabled to transmit its acquired stormwater data, either directly or indirectly, to one or more remote computing devices that is hosting a stormwater monitoring application (SMA). The SMA is enabled to process and analyze the stormwater data. The SMA generates measurements and reports based on the processed and analyzed stormwater data.

1 Claim, 11 Drawing Sheets

Related U.S. Application Data

(60) Provisional application No. 62/321,011, filed on Apr. 11, 2016, provisional application No. 62/319,084, filed on Apr. 6, 2016.

(51) Int. Cl.
    *E03F 1/00*     (2006.01)
    *G01N 33/18*     (2006.01)
    *G01K 13/02*     (2006.01)
    *G01F 1/00*     (2006.01)
    *G01F 1/66*     (2006.01)
    *G01F 15/06*     (2006.01)

(56) References Cited

U.S. PATENT DOCUMENTS

| | | | |
|---|---|---|---|
| 5,942,698 A * | 8/1999 | Stevens | G01F 1/002 340/606 |
| 6,975,236 B2 | 12/2005 | Staples | |
| 7,104,116 B2 | 9/2006 | Discenzo | |
| 7,114,388 B1 * | 10/2006 | French | G01W 1/00 73/170.16 |
| 7,230,528 B2 | 6/2007 | Kates | |
| 7,275,420 B2 | 10/2007 | Discenzo | |
| 7,360,413 B2 | 4/2008 | Jeffries et al. | |
| 7,439,867 B2 | 10/2008 | Staples | |
| 7,581,434 B1 | 9/2009 | Discenzo et al. | |
| 8,286,512 B1 * | 10/2012 | Selbig | G01N 1/16 73/863.41 |
| 8,489,342 B2 | 7/2013 | Dugger et al. | |
| 8,591,147 B2 | 11/2013 | Quigley et al. | |
| 8,610,586 B2 | 12/2013 | Shimada et al. | |
| 9,410,833 B1 | 8/2016 | Leaders et al. | |
| 9,631,356 B2 | 4/2017 | Nesbitt et al. | |
| 9,772,609 B2 | 9/2017 | Goodman et al. | |
| 9,874,466 B2 | 1/2018 | Leaders et al. | |
| 2006/0270915 A1 | 11/2006 | Ritter et al. | |
| 2007/0103324 A1 * | 5/2007 | Kosuge | E03F 7/00 340/618 |
| 2008/0060430 A1 * | 3/2008 | Galloway | G01F 23/0061 73/290 R |
| 2009/0168703 A1 * | 7/2009 | Pandey | H04W 8/005 370/329 |
| 2009/0237212 A1 | 9/2009 | Hyde et al. | |
| 2011/0285516 A1 | 11/2011 | Ritter | |
| 2011/0303004 A1 * | 12/2011 | Carson-Rowland | G01F 23/24 73/304 R |
| 2013/0317766 A1 * | 11/2013 | Decker | G01F 23/0076 702/55 |
| 2014/0111349 A1 | 4/2014 | Roberson et al. | |
| 2014/0324406 A1 * | 10/2014 | Nesbitt | E03F 3/00 703/9 |
| 2014/0351311 A1 * | 11/2014 | Nakatsugawa | H04L 67/10 709/201 |
| 2015/0174732 A1 | 6/2015 | Raghavan et al. | |
| 2015/0342169 A1 | 12/2015 | Zeevi | |
| 2015/0355045 A1 * | 12/2015 | Solomon | F17D 5/02 702/36 |
| 2017/0227391 A1 * | 8/2017 | Forster-Knight | E02D 29/12 |
| 2017/0311574 A1 * | 11/2017 | Swan | A01K 29/005 |

* cited by examiner

DISTRIBUTED SYSTEMS FOR STORMWATER MONITORING AND REPORTING

CROSS REFERENCE TO RELATED APPLICATIONS

The application claims priority to U.S. Nonprovisional patent application Ser. No. 15/480,084, filed on Apr. 5, 2017, entitled DISTRIBUTED SYSTEMS FOR STORMWATER MONITORING AND REPORTING, the entirety of the contents herein incorporated.

The application claims priority to U.S. Provisional Patent Application No. 62/319,084, filed on Apr. 6, 2016, entitled STORMWATER MONITORING SYSTEM, the entirety of the contents herein incorporated.

The application also claims priority to U.S. Provisional Patent Application No. 62/321,011, filed on Apr. 11, 2016, entitled SCREEN DESIGN, FLOW CHANNEL, SENSOR ARRAY FOR FLOW-THROUGH STORMWATER MONITORING HARDWARE, the entirety of the contents herein incorporated.

BACKGROUND

Stormwater drainage systems (e.g. storm drains and sewers) are employed to redirect excess rain and ground water from impervious surfaces through a network of flow paths and/or flow channels. Such flow paths and/or channels are typically constructed via cavities, flow paths, or flow channels within pipes, tunnels, gutter, and the like. The stormwater may be redirected into nearby rivers, streams, or other waterways via such stormwater drainage systems. Due to the passive nature of collecting and transporting water in pipes, tunnels, and gutters, stormwater drainage systems are susceptible to clogging via debris and/or sediments. Furthermore, such passive systems may introduce the debris, sediments, or even contaminants into rivers, streams, and other waterways. Accordingly, it is desirous to monitor various properties of stormwater flowing through stormwater drainage systems. It is for these and other concerns that the following disclosure is provided.

SUMMARY

Embodiments of the present invention are directed towards methods and systems for automatically monitoring and reporting on stormwater. On such exemplary embodiment includes providing, to a data-collection device, a configuration for the data-collection device and for each of multiple stormwater sensor nodes or sensor devices. The data-collection device may be a controller node. The configuration for the data-collection device and/or a configuration for each of the sensor devices may be a transmitter-receiver pair. For instance, the configuration for the data-collection device may include at least a data-transmission frequency and a defined data-transmission channel. The configuration for the sensor devices may include a data-acquisition frequency and another data-transmission frequency. The data-transmission frequency for the sensor devices and the data-collection devices may be equivalent, similar, or dissimilar.

The data-collection device is employed to provide the stormwater sensor devices at least a portion of the configurations. Each of the stormwater sensor devices is employed to iteratively acquire stormwater data. Stormwater data may be acquired at a particular stormwater sensor at a rate that is based on the data-acquisition rate for the corresponding stormwater sensor devices. The stormwater sensor devices are employed to provide the stormwater data to the data-collection device. For instance, the stormwater sensor device may provide the stormwater data to the data-collection device at a rate based on the data-transmission rate for the stormwater sensor device.

The data-collection device is employed to aggregate the stormwater data that is acquired form the stormwater sensor devices. The data-collection device is employed to periodically provide a user-computing device the aggregated stormwater data at a rate based on the data-transmission rate for the data-collection device. The user computer may be running and/or hosting a stormwater monitoring application (SMA) that is employed to receive the stormwater data and generate one or more stormwater reports or visualizations based on the measured stormwater data. For instance, the stormwater measurement may be a site-level stormwater measurement. A display device of the user-computing device may provide a visualization (e.g. a plot, graph, chart, or the like) of the stormwater measurements.

In various embodiments, the method further includes receiving a geo-location and a sensor identifier for each of the stormwater sensor devices. A sensor identifier may include a unique code, number, string, or other identifying nomenclature for the sensor device. The geo-location and the sensor identifier are associated and stored. For instance, the association between the geo-location and sensor identifier may be stored in a registration for the sensor device.

The user-computing device may be employed to generate a report based on the stormwater measurements. Furthermore, the user-computing device may be employed to provide the report to a user. The stormwater sensor devices may include various sensors, such as but not limited to fluid flow rate sensors, fluid pH-level sensors, fluid temperature sensors, or the like.

In some non-limiting embodiments, the stormwater sensor devices are stormwater sensor nodes that are configured and/or arranged in a mesh network. The mesh network may be a self-healing mesh network. The data-collection device may be a controller node the mesh network. The stormwater sensor device may be distributed across a portion of a stormwater drainage system. The method may employ the user-computing device to determine a Gauckler-Manning coefficient associated with the stormwater drainage system. The determination of the coefficient may be based on the stormwater data.

DETAILED DESCRIPTION

Figure 1:
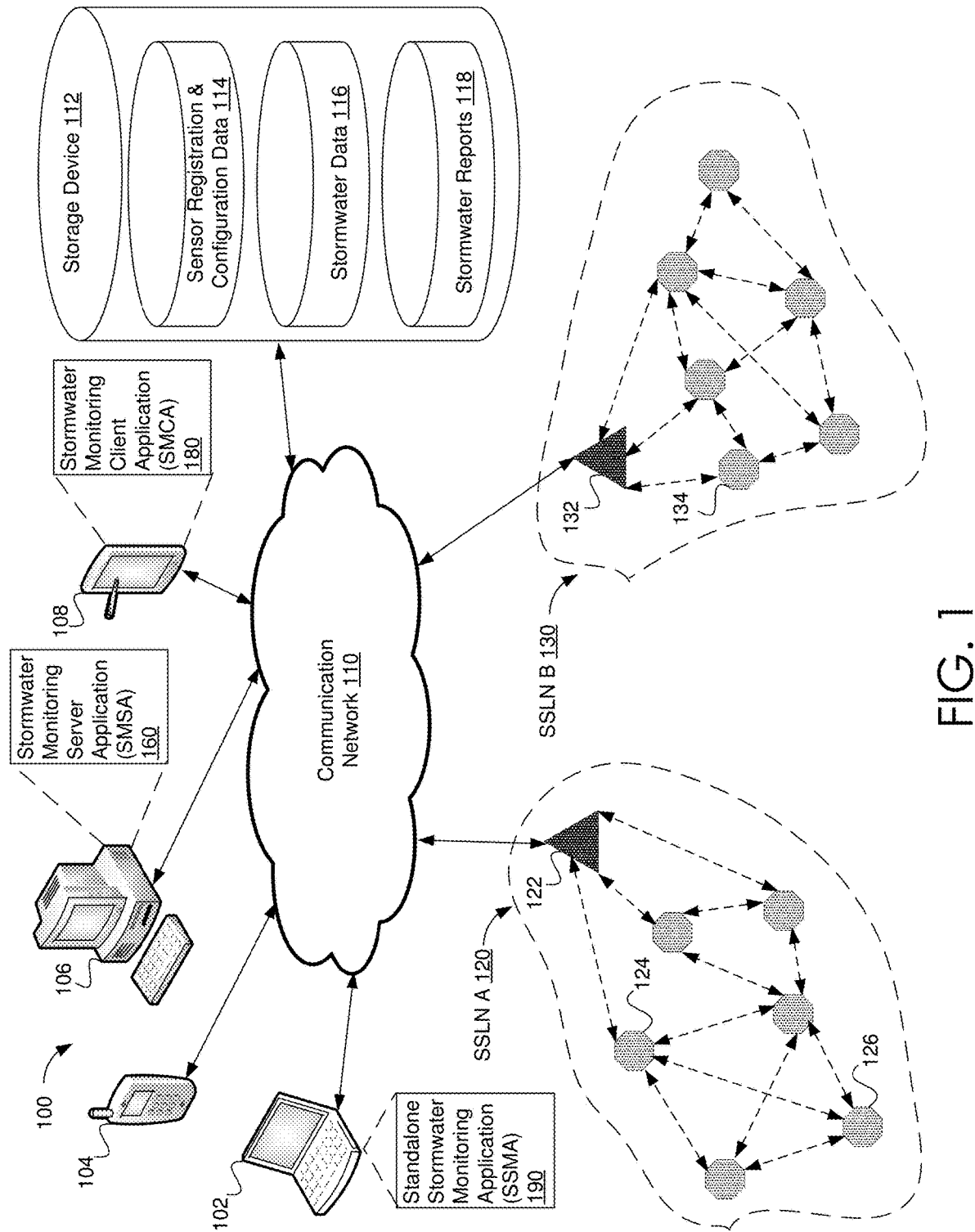
FIG. 1 illustrates an exemplary embodiment of a distributed system enabled to simultaneously and actively monitor stormwater across multiple remote locations, acquire, aggregate, and analyze stormwater data from the multiple locations, and generate stormwater reports and notifications based on the stormwater data analysis that is consistent with the various embodiments discussed herein.

Briefly stated, various embodiments are directed towards systems and methods for the automatic monitoring and reporting of data relating to the chemistry and flow of stormwater (i.e. stormwater data). Although the various embodiments discussed herein are directed towards monitoring, analyzing, and reporting of data related to stormwater, it should be understood that the monitored fluid is not limited to stormwater. That is, the various systems and methods disclosed may readily monitor various properties of any flowing liquid and/or gaseous fluid, including but not limited to stormwater, rainwater, and the like. Such monitored fluid properties include but are not otherwise limited to fluid volume, fluid flow rate, fluid turbidity, fluid pH-level, fluid viscosity, fluid temperature, fluid velocity, fluid depth, and the like. Virtually any property of any fluid, including the chemistry of the fluid, may be monitored and reported on via the various embodiments.

More specifically, multiple fluid sensors are exposed to stormwater via positioning the sensors in locations of interest, e.g. within cavities of stormwater drainage systems. Locations of interest may include locations where it is desirable to acquire data relating to the rainfall and/or stormwater flowing through the location. In various embodiments, fluid sensors are placed within the cavities or fluid flow paths (or channels) of pipes, tunnels, gutters, and the like of stormwater drainage systems. The sensors may be enabled to acquire stormwater data indicating any of the various fluid properties that are desired to monitor. In embodiments, the various sensors may be integrated and/or embedded into a sensor array. The sensor array may be integrated and/or embed into a sensor device and exposed to fluid flowing through the stormwater drainage system.

A sensor device may be enabled to transmit its acquired stormwater data, either directly or indirectly, to one or more remote computing devices. In some embodiments, a sensor device is enabled to receive stormwater data from other sensor devices. Such a sensor device may repeat, route, and/or relay the stormwater data that is received from other sensor devices to other devices, such as but not limited to still other sensor devices and/or remote computing devices.

The sensor devices may be arranged into nodes of one or more networks of sensors. Thus, a sensor device may be a sensor node. The networks may be localized to specific areas, regions, and/or locations of interest. In such embodiments, a network of stormwater sensor devices may be referred to as a stormwater sensor localized-network (SSLN). A single SSLN may include multiple sensor nodes distributed throughout the area and/or region "covered" by the SSLN. There is virtually no upper bound to the total number of sensor nodes included in a single SSLN. An essential functionality of a SSLN is that the SSLN is enabled to provide at least a portion of the stormwater data acquired by at least a portion of its sensor nodes to one or more devices and/or nodes not included in the SSLN. Multiple SSLN may be arranged and/or constructed to cover unlimited, disparate, contiguous, and/or non-contiguous areas, locations, and/or regions of the planet.

For instance, in one non-limiting embodiment, a first SSLN is located to provide stormwater-monitoring coverage across a first portion of a municipal stormwater drainage system that services one region (e.g. a neighborhood) of the municipality. A second SSLN is located to provide stormwater-monitoring coverage across a second portion of the drainage system that services a second region of the municipality. The first SSLN includes a plurality of sensor nodes (e.g. 10 sensor nodes) that is strategically distributed within the first portion of the stormwater drainage systems that services the first region. The second SSLN may include another plurality of sensor nodes (e.g. 20 sensor nodes) that is strategically distributed within the second portion of the stormwater drainage systems that services the second region. In some embodiments, an overlap (or intersection) exists for multiple SSLNs in the areas that the individual SSLN cover when acquiring stormwater and/or transmitting data. In other embodiments, multiple SSLNs are distinct, and no intersection exists in the areas of coverage for multiple SSLNs.

multiple SSLN may provide at least some partial overlap in the coverage for acquiring stormwater data. In other embodiments, the area for A SSLN may include a controller node. In such embodiments, the sensor nodes of a SSLN are enabled to transmit, either directly or indirectly, their acquired stormwater data to a controller node included in the SSLN. The controller node is enabled to aggregate the stormwater data from each of the sensor nodes and transmit the aggregated stormwater data to the one or more remote computing devices. Because the controller node aggregates stormwater data from the plurality of nodes, the controller node may be a data-collection device. In other embodiments, at least a portion of the sensor nodes are enabled to transmit their acquired stormwater data directly to one or more remote computing devices and/or nodes of other SSLNs.

In various embodiments, a SSLN may employ a mesh network topology, i.e. an SSLN may be a mesh network. In such embodiments, at least a portion of the sensor nodes, in addition to acquiring stormwater data, may serve as a repeater, router, and/or relay data transmitting device for transmitting the stormwater data acquired by other sensor nodes to the controller node of the SSLN. Various redundancies may be employed in such mesh SSLNs. That is, self-healing techniques may be employed such that the loss of one or more sensor nodes in a particular SSLN does not degrade the operation and/or functionality of the particular SSLN. Such SSLNs may be referred to as self-healing SSLNs.

In some embodiments, a controller node of an SSLN is enabled to transmit stormwater data to a controller node of another SSLN. In this way, a network of SSLNs may be employed. Such SSLN may serve as a repeater, router, and/or relay data transmitting network, i.e. one SSLN may relay, route, and/or repeat the stormwater data acquired by another SSLN. For instance, a mesh network of SSLNs may be constructed. Again, various self-healing techniques may be employed to enable a self-healing mesh network of self-healing mesh SSLNs.

One or more remote computing devices are enabled to receive stormwater data acquired by the sensor nodes of one or more SSLNs, from the controller nodes of the one or more SSLNs. Furthermore, such remote computing devices are enabled to register, configure, operate, and control the deployed sensor nodes, as well as monitor, maintain, and operate an unlimited number of SSLNs. A remote computing device is further enabled to automatically aggregate, process, and analyze the stormwater data from multiple SSLNs, as well as automatically generate visualizations (i.e. plots, charts, graphs, and the like), reports, and other documents documenting the results of the acquisition and analysis of the stormwater data. The stormwater data, as well as the results of the stormwater data analysis and any documents documenting the results may be automatically logged and/or stored on data storage devices. Such logged stormwater data and stormwater reports may be later retrieved for further analysis and/or review. The computing devices configuring and controlling the SSLNs, as well as the data storage devices storing the stormwater data and data analysis results may be distributed across a stormwater monitoring system and/or platform. For instance, the services and/or functionalities of the stormwater monitoring system may be accessed as cloud-based services and/or web-based services and/or functionalities.

Exemplary Stormwater Monitoring System

FIG. 1 illustrates an exemplary embodiment of a distributed system 100 enabled to simultaneously and actively monitor stormwater, as well as other fluids, across multiple remote locations, areas, regions, and the like that is consistent with the various embodiments discussed herein. Thus, distributed system 100 is a stormwater monitoring system. More specifically, system 100 acquires, aggregates, and analyzes stormwater data from the multiple remote locations, areas, regions, and the like. System 100 may log and/or archive the (analyzed and/or raw) stormwater data, as well as generate stormwater reports and notifications based on the stormwater data analysis.

System 100 includes various user-computing devices, such as but not limited to laptop 102, smartphone 104, desktop 106, tablet 108, and the like. In other embodiments, system 100 may include more or less user-computing devices. For instance, system 100 may include additional mobile devices, wearable devices, and the like. An exemplary, but non-limiting embodiment of a computing device is discussed in conjunction with at least computing device 800 of FIG. 8. However briefly, a computing device may be referred to as a processor device because a computing device generally employs and/or includes a processor. A generalized communication network, such as but not limited to communication network 110, may communicatively couple at least a portion of user-computing devices 102-108.

Communication network 110 may be any communication network, including virtually any wired and or wireless communication technologies, wired and/or wireless communication protocols, and the like. It should be understood that communication network 110 may be virtually any communication network that communicatively couples a plurality of computing devices in such a way as to enable users of computing devices to exchange information via the computing devices.

System 100 may include one or more storage devices, such as but not limited to storage device 112. Storage device 112 may include volatile and non-volatile storage devices for digital data storage. Storage device 114 may include non-transitory storage media, such as but not limited to magnetic and/or optical disks, magnetic tape, solid-state storage media, and the like. Communication network 110 may communicatively couple storage device 112 to at least a portion of user-computing devices 102-108. In some embodiments, storage device 112 may be a logical storage device logically distributed over multiple physical storage devices. Thus, storage device 112 may be a virtualized storage device. For instance, one or more "cloud storage" services and/or service providers may provide, implement, and/or enable storage device 112.

Storage device 112 may store various data, including but not limited to sensor registration and configuration data 114, stormwater data 116, and stormwater reports 118. Storage device 112 may store machine-, processor-, and/or computer-executable instructions, such as but not limited to instructions, that when executed, enabled the actions, steps, operations, or functionalities of various applications, such as but not limited to stormwater monitoring application (SMA). Such SMAs include, but are not otherwise limited to server application (SMSA) 160, stormwater monitoring client application (SMCA) 180, standalone stormwater monitoring application (SSMA), and the like.

In some embodiments, a server-client architecture is employed. As shown in FIG. 1, desktop 106 is running and/or hosting SMSA 160 and tablet 108 is running and/or hosting SMCA 180. Thus, desktop 106 may be a server-computing device and tablet 108 may be a client-computing device. Other embodiments are not so constrained, and virtually any computing device may run and/or host either SMSA 160 and/or SMCA 180. In some embodiments, SMSA 160 may be run on a web-based and/or cloud-based server. Thus, the functionalities and/or services of system 100 may be accessed via web-based and/or cloud-based services and/or functionalities.

In other embodiments, a server-client architecture is not employed. That is, the functionalities and operations of SMSA 160 and SMCA 180 may be integrated and/or embedded within a single application, i.e. a standalone application. For instance, a single standalone application, such as but not limited to standalone stormwater monitoring application (SSMA) 190 may provide all of the functionalities associated with the combination of SMSA 160 and SMCA 180. FIG. 1 shows laptop 102 hosting and/or running SSMA 190, although other embodiments are not so constrained. Virtually any computing device may run, host, and/or execute any of SMSA 160, SMCA 180, and/or SSMA 190.

Although FIG. 1 shows SMAs running on a single computing device, SMSA 160, SMCA 180, SSMA 190, or any other application may be distributed across multiple physical computing devices. In some embodiments, at least a portion of such applications may be hosted and/or running on one or more virtual machines (VMs), implemented by virtually any computing device, such as but not limited to user-computing devices 102-108.

System 100 includes one or more stormwater sensor localized-networks (SSLN). As shown in FIG. 1, system 100 includes two SSLNs: SSLN A 120 and SSLN B 130. Other embodiments are not so constrained, i.e. other embodiments may include fewer or more SSLNs than system 100. Each SSLN may include at least one controller node and one or more sensor nodes. For instance, SSLN A 120 includes controller node 122 and six sensor nodes, such as but not limited to sensor node 124. Similarly, SSLN B 130 includes controller node 132 and six sensor nodes, such as but not limited to sensor node 134.

There is no upper bound to the number of controller nodes and sensor nodes included in a single SSLN. The number of controller nodes and sensor nodes may be scaled based on the number of stormwater measurement locations and the required bandwidth for data transmission. Furthermore, embodiments of such a system may include fewer or more than two SSLN. There is no upper bound to the number of SSLNs that may be included in system 100. Various embodiments of controller nodes are discussed in conjunction with at least controller node 270 of FIG. 2C.

Various embodiments of sensor nodes are discussed in conjunction with at least sensor nodes 200, 250, and 300 if FIGS. 2A, 2B, and 3A-3B respectively. However, briefly here, the sensor nodes may include a plurality of fluid sensors, such as but not limited fluid flow-rate sensors, temperature sensors, turbidity sensors, pH-level sensors, and the like. The plurality of sensors may be embedded and/or integrated in a sensor array. The sensor nodes may be deployed in a remote location of interest to acquire stormwater data and/or measurements via the various sensors within the sensor array. When deployed, the various fluid sensors may be configured to be exposed to stormwater other another fluid. The sensors sample the fluid and make measurements of the various properties of the fluid. When the fluid is flowing stormwater, the data generated via the sensors of the sensor nodes is referred to as "stormwater data." The sensor nodes acquire stormwater data.

Each sensor node within a SSLN may wirelessly and/or via wired-communication transmit the acquired stormwater data to a controller node (or to another sensor node) of the SSLN. The controller node may aggregate the stormwater data from the plurality of sensor nodes. Because the controller node aggregates stormwater data from the plurality of nodes, the controller node may be a data-collection device. The controller node may provide aggregated the stormwater data to a SMA, such as but not limited to SMSA 160, SMCA 180, SSMA 190, or the like, for stormwater data processing, analysis, visualization, storage, and/or reporting.

Turning the attention to the topologies of a SSLN and the communication (i.e. data/information transmission) inter and intra-SSLNs, as used herein, "local-data transmission" refers to the transmission of any information, including but not limited to stormwater data, sensor node configurations, and the acquisition/transmission frequencies a between nodes (i.e. sensor and/or controller nodes) within a single SSLN. Accordingly, local-data transmission refers to the transmission of information between the sensor nodes of a SSLN and/or between the sensor nodes and one or more controller nodes of the SSLN. Local-data transmission and/or local-communication channels are shown within SSLN A/B 120/130 via the hashed bi-directional communication arrows.

In contrast to local-data transmission, "remote-data transmission" refers to the transmission of any information from a (sensor and/or controller) node within a SSLN to a (sensor and/or controller) node outside the SSLN and/or a computing device outside the SSLN and/or from a node/computing device outside the SSLN to a node within the SSLN. Remote-data transmission may refer to the transmission of information and/or data between a sensor/controller node and communication network 110. Remote-data transmission and/or remote-communication channels are shown between controller nodes 122/132 and communication network 110 via the solid bi-directional communication arrows. In the various embodiments, each SSLN is enabled for both local-data transmission and remote-data transmission.

In some embodiments, to enable remote-data transmissions between user-computing devices and an SSLN, at least one of the one or more controller nodes in each SSLN is communicatively coupled to a communication network 110, as shown in FIG. 1 (and indicated by the remote-data transmission solid bi-directional arrows between controller nodes 122/132 and communication network 110). Accordingly, to enable remote-data transmissions, each SSLN includes at least one controller node that is communicatively coupled to at least one of SMSA 160, SMCA 180, and/or SSMA 190, via communication network 110. As discussed in conjunction with at least controller node 270 of FIG. 2C, a controller node may include one or more onboard data transmitter devices to enable remote-data transmission thru communication network 110. Such onboard data transmitter devices may include remote-data transmitter devices.

Furthermore, to enable local-data transmission within a SSLN, each sensor node in a SSLN is either directly and/or indirectly communicatively coupled to at least the controller node of the SSLN that is communicatively coupled to communication network 110 (and indicated by the local-data transmission hashed bi-directional arrows within SSLN A/B 120/130). As discussed in conjunction with at least sensor node 200 of FIG. 2A, a sensor node may include one or more onboard data transmitter devices to enable local-data transmission thru with other sensor nodes and one or more controller nodes. Such onboard data transmitter devices may include local-data transmitter devices.

In various embodiments, in addition to the remote-data transmitter devices, a controller node may include local-data transmitter devices to enable local-data transmission between a controller node and sensor nodes of the SSLN (or other controller nodes of the SSLN). Thus, in the various embodiments, a controller node may employ remote-data transmission devices to communicate with devices outside of its own SSLN and employ local-data transmission devices to communicate with nodes within its own SSLN.

Local-data transmission and remote-data transmission may be enabled via separate communication protocols and/or (wired and/or wireless) communication devices. For instance, remote-data transmission may employ various internet protocols, such as but not limited to any of the common TCP/IP protocols. Remote-data transmission devices may include virtually any communication devices, such as but not limited to WiFi-enabled devices, Ethernet-enabled devices, Bluetooth-enabled devices, USB-enabled devices, optical data transmission enabled-devices, and the like. Local-data transmission devices may include virtually any (wired and/or wireless) communication devices, such as but not limited to radio-frequency (RF) wireless transmission-enabled devices. It should be understood that wireless local-data transmission devices may employ communication bands other than RF-bands. In some embodiments, local-data transmission devices may be associated with smaller communication (spatial) ranges than corresponding remote-data transmission. Thus, local-data transmission may be referred to as "short-range" data transmission and/or communication and remote-data transmission may be referred to as "long-range" data transmission.

As discussed above, sensor nodes acquire stormwater data via various embedded fluid sensors. The stormwater data from each sensor node is relayed and/or routed (either directly or indirectly via one or more other sensor nodes) to one or more controller nodes (via local-data transmission). The controller nodes can then act as a communication relay, repeater, and/or router to provide the stormwater data to SMSA 160, SMCA 180, and/or the SSMA 190 (via remote-data transmission). As used herein, "indirect" data transmission between two nodes is local-data transmission between two nodes of a SSLN when one or more other nodes is "between" the two communication nodes and the one or more other nodes acts as a transmission relay, router, and/or repeater between the two communicating nodes. That is, the two communicating nodes are "indirectly communicatively coupled."

In contrast to indirect transmission and/or communication of data, "direct" data transmission is local-data transmission between two nodes of a SSLN with no other node in "between" the communicating nodes, i.e. the two communicating nodes are paired for communication. That is, the two communicating nodes are "directly communicatively coupled." Local-data transmission may occur in broadcast mode.

In some embodiments, each sensor node is directly communicatively coupled to a controller node. In other embodiments, one or more sensor nodes are indirectly communicatively coupled to the controller node. In such embodiments, if not directly communicatively coupled to a controller node, then a sensor node is indirectly communicatively coupled to a controller node via other sensor nodes. That is, as shown in FIG. 1, sensor node 124 may serve as a data transmission relay, router, and/or repeater between a sensor node 126 and controller node 122 of SSLN A 120. Note that sensor node 126 is indirectly communicatively coupled to controller node 122 and sensor node 124 is directly communicatively coupled to controller node 122. In the various embodiments, each sensor node is directly communicatively coupled to at least one other sensor node that is either indirectly (and/or directly) communicatively coupled to the controller node via one or more "hops" through other sensor nodes. Thus, in some embodiments, an SSLN may be arranged in a mesh network topology, i.e. an SSLN may be a mesh network.

In some embodiments, a mesh SSLN may be a "self-healing" communication network. That is, various mesh self-healing techniques, algorithms, network topologies may be employed to include various redundant communication routes to avoid the degradation of network performance in response to the loss of one or more nodes of the mesh network. For instance, the communicative coupling between the sensor nodes may be such that the loss of a single sensor node will not isolate (data transmission-wise) any other sensor node from a controller node that is enabled for remote-data transmission. As shown in FIG. 1, via the bi-directional local-data communication channels (hashed bi-directional arrows), the loss of any single sensor node in either SSLN 120 and/or SSLN 130 will not isolate any sensor node from the corresponding controller node in the SSLN.

In some embodiments, the sensor nodes and/or the controller nodes include logic devices that actively monitor and manage network performance. The sensor and/or controller nodes may act as an active router that bases their routing of data transmission on a current state of the self-healing mesh SSLN, i.e. which, if any sensor nodes have ceased operating.

By employing differing mesh network topologies and self-healing techniques that employ differing levels of redundancy in the communicative coupling of the nodes, virtually any level of data-transmission redundancy may be achieved in a SSLN. That is, a self-healing mesh SSLN may lose up M sensor nodes without isolating any other remaining sensor nodes from a controller node, where M is a positive integer that is less than integer N, the number of sensor nodes included in the SSLN. As shown in FIG. 1, in such self-healing mesh network topologies, each sensor node may be communicatively coupled to two or more other sensor nodes and each controller node is communicatively coupled to two or more sensor nodes. The network topology of a SSLN may include virtually any topology with the required level of local-data transmission redundancy for the particular application. Accordingly, a SSLN may include virtually any mesh network topology.

Turning attention to the functionalities and operation of an SMA, in addition to processing the stormwater data, an SMA may manage and maintain each of the SSLNs that are acquiring and providing stormwater data. More specifically, one or more SMAs may be employed by a user to register and configure each of the controller nodes and each of the sensor nodes of the SSLNs. Registering the sensor nodes and controller nodes may include storing a geo-location and a sensor identification for each sensor node in sensor registration and configuration data 114 (or another storage location). The geo-location and/or the sensor identification may be manually provided by a user of the SMA and/or automatically determined. For instance, onboard global positioning devices may be included in the sensor/controller nodes. Furthermore, a unique identifier may be included in the sensor/controller nodes. The sensor nodes may be automatically interrogated to determine such registration information.

In addition to registering the sensor nodes, the SMA may be employed to configure the sensor nodes and the controller nodes. The configuration of the controller and the sensor nodes may be stored in sensor registration and configuration data 114. The configuration of a sensor node may include at least a data-acquisition frequency and a (sensor node) data-transmission frequency. The data-acquisition frequency may be the frequency that a sensor nodes acquires stormwater data. For instance, the data-acquisition of a sensor node may be acquired data once and hour. Similarly, the configuration of a controller node may include a (controller node) data-transmission frequency, that indicates the frequency that the aggregated stormwater data is provided to the SMA.

In addition to acquiring data at the data-acquisition frequency, a sensor node may acquire stormwater data if one or more predetermined flow-event thresholds are detected. That is, stormwater data may be acquired when a sensor of a sensor node detects a signal greater than a threshold level. In various embodiments, a sensor node may acquire stormwater data when a flow event is received at the sensor node. A flow event may be received at the sensor node if it is time to acquire stormwater data (based on the data-acquisition frequency) or when one or more flow-event thresholds are exceed.

The SMA may provide each sensor node its sensor node configuration via the controller node. The controller node may then provide each sensor node its configuration via local-data transmission around the SSLN. In some embodiments, a data-transmission pipeline is generated and maintained by the SMW. A controller node may request the its sensor node configuration, as well as its sensor node configurations of other sensor nodes. The controller node and sensor node configurations may be provided to the controller node via the data-transmission pipeline. Furthermore, each of the sensor nodes may request its configuration from the controller node. For instance, a sensor node may be scheduled to periodically inquire regarding its configurations. In response to the request, the controller node may answer by providing the sensor node its sensor node configuration via the mesh network topology. Upon receiving the response from a controller node, the sensor node may update its local configuration and/or settings.

A sensor node may continue to acquire stormwater data for each flow event. At the end of each data-transmission cycle, a sensor node may transmit the acquired stormwater data to the controller node via the mesh network. In various embodiments, a plurality of flow events may occur between data-transmission cycles, i.e. a sensor node may buffer stormwater data. The sensor node may package and transmit the stormwater data in data packets to the controller node.

The controller aggregates the stormwater data packets from each of the sensor nodes. In addition to stormwater data, the data packets may include the associated sensor nodes identification, timestamp, geo-location, or any other metadata associated with the measurement of the stormwater's various properties. The aggregated stormwater data may be buffered and/or temporally stored by the controller node. At the end of a data-transmission cycle of the controller node, the controller node may transmit the stormwater data to the SMA. Note that the data-transmission frequency of the controller node may be different than the data-transmission frequency of the sensor nodes. In some embodiments, the controller node provides the aggregated stormwater data to the SMA in response to a data request from the SMA.

The SMA may enable the storing or archiving of the stormwater data packets. For instance, the stormwater data packets may be stored in stormwater data 116 of FIG. 1. The SMA may aggregate the stormwater data over multiple data-transmission cycles. For instance, the SMA may aggregate stormwater data over several days, weeks, or virtually any temporal period. The SMA may aggregate stormwater data from multiple SSLNs.

In various embodiments, the SMA may process and analyze the aggregated stormwater data. For instance, the SMA may normalize the stormwater data, as well as calibrate the stormwater data. In various embodiments, the SMAA may determine various stormwater metric based on the normalized and calibrated data. For instance, the SMA may determine a Gauckler-Manning coefficient for the stormwater drainage system based on the stormwater data. For instance, the Gauckler-Manning formula, shown below may be employed to determine the Gauckler-Manning coefficient (n).

$$V = \frac{k}{n} R_h^{2/3} S^{1/2},$$

where V is the cross-sectional average velocity of the flowing stormwater, Rh is the hydraulic radius, S is the slope of the hydraulic grade line (i.e. channel bed slope when the water depth is constant), and k is a conversion factor.

For each SSLN, the SMA may combine the corresponding stormwater metrics to generate one or more site-level stormwater measurements. A site-level stormwater measurement may correspond to stormwater measurements for the sit covered by the SSLN. For instance, the stormwater metrics may be combined to generate a site-level average flow rate, average flow volume, or the like.

The SMA may actively monitor one or more stormwater trigger conditions. A user notification may be provided to a user if a stormwater condition is triggered. For instance, if a pH-level of the stormwater exceeds as pH-threshold, based on the stormwater data, the SMA may provide a notification to a user. The SMA may automatically generate visualizations (i.e. plots, charts, graphs, and the like) of the site-level storm measurements. A display device of a user-computing device may be employed to display such visualizations. An SMA may automatically generate stormwater reports, and other documents documenting the results of the acquisition and analysis of the stormwater data, including the stormwater site-level measurements. Such stormwater reports may be stored in stormwater reports 118 of FIG. 1.

Sensor and Controller Nodes of Stormwater Sensor Localized Networks

Figure 2A:
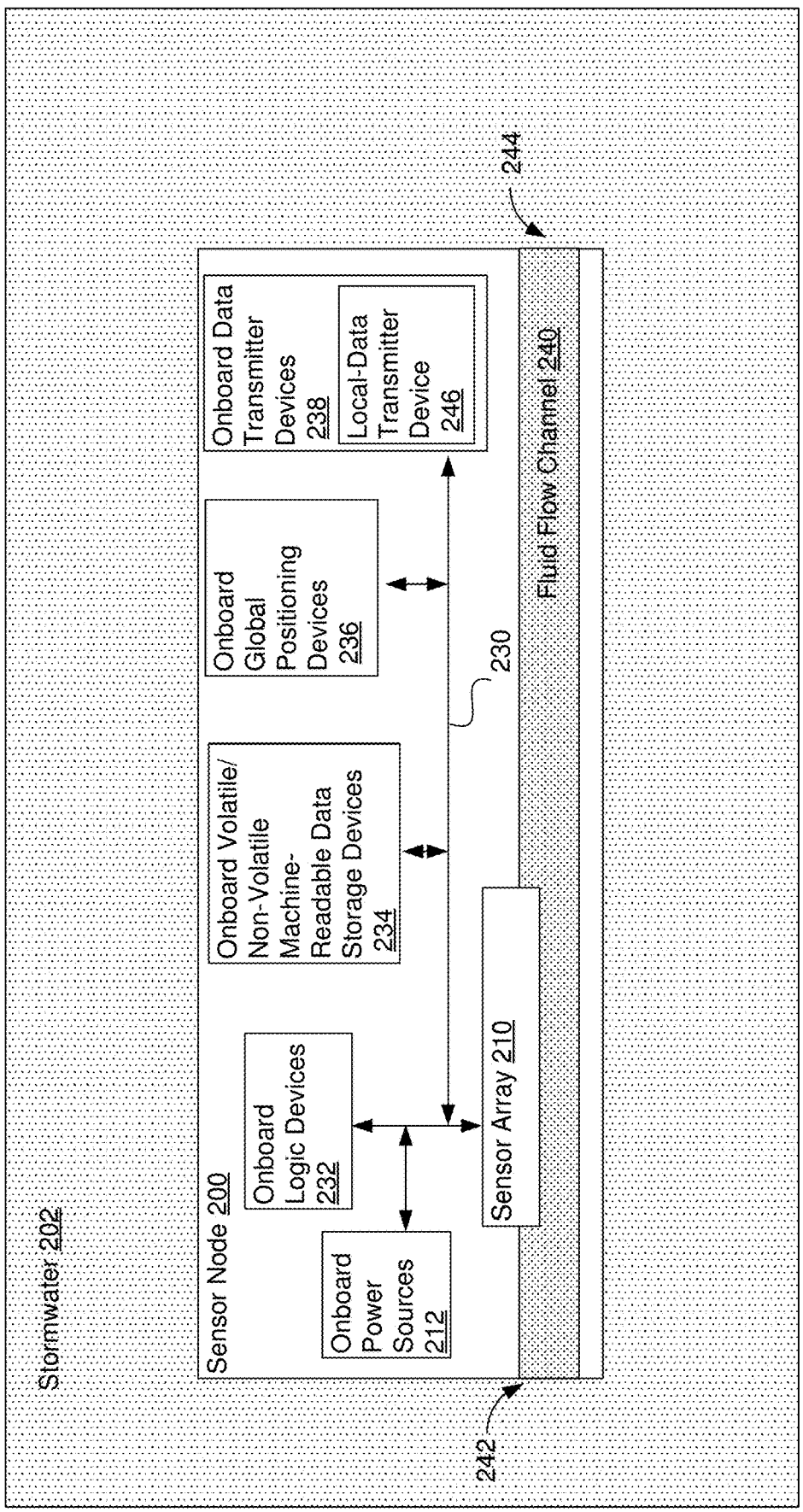
FIG. 2A schematically illustrates an exemplary embodiment of a sensor node that may be employed in the system of FIG. 1.

FIG. 2A schematically illustrates an exemplary embodiment of remote sensor node 200 that may be employed in the system 100 of FIG. 1. Sensor node 200 may be a fluid sensor node. In some embodiments, sensor node 200 is a stormwater sensor node. That is, sensor node 200 may be employed as a sensor node within a stormwater sensor localized-network (SSLN), such as but not limited to SSLN A 120 and/or SSLN B 130 of FIG. 1. For instance, fluid sensor node 200 may be employed as any of sensor nodes 124, 126, and/or 134.

Sensor node 200 may be exposed to stormwater 202 or any other liquid or gaseous fluid. Sensor node may include a fluid inlet 242, a fluid outlet 244, and a fluid flow channel 240 between the fluid inlet 242 and the fluid outlet 244. Sensor node 200 may include a sensor array 210 that exposes one or more fluid sensors to fluid flowing in fluid flow channel 240. Such fluid sensors included in sensor array 210 may include but are not limited to fluid flow-rate sensors, temperature sensors, turbidity sensors, pH-level sensors, and the like. The various sensors may sense various properties of the fluid flowing through fluid flow channel 240.

Sensor node 200 may include onboard power sources 212, such as but not limited to rechargeable and/or replaceable batteries to provide DC and/or AC (in combination with a power inverter) power to the various other components, devices, and sensors of sensor node 200. Sensor node 200 may include one or more onboard logic devices. Such logic devices include, but are not otherwise limited to microprocessors, microcontrollers, central processing units (CPUs), field programmable gate arrays (FPGAs), application specific integrated circuits (ASICs), systems-on-a-chip (SOC), and the like. Such logic devices may perform the operations and/steps that control the sensors, as well as other components and devices included in sensor node 200. In some embodiments, the logic devices may perform data transmission routing operations.

Sensor node 200 may additionally include various onboard volatile and/or non-volatile machine-readable data storage devices 234 to at least temporally store, buffer, and/or cache data, such as but not limited to data generated via sensor array 210. Such data storage devices include, but are not otherwise limited to SRAM devices, (S)DRAM devices, EEPROM devices, FLASH devices, and the like. Sensor node 200 may include one or more onboard global positioning devices 236. Such global positioning devices 236 may include global positioning satellite (GPS) receivers to determine the geo-coordinates of a geo-location of sensor node 200.

Sensor node 200 may also include onboard data transmitter devices 238 to provide and receive (i.e. transmits) information, such as but not limited to stormwater data. Data transmitter devices 238 may enable data transmission. For instance, onboard transmitter devices 238 includes local-data transmitter devices 246, which enables local-data transmission within a SSLN. For instance, local-data transmitter devices 246 may include radio-frequency (RF) data-transmission devices. Note that each of these devices, components, sensors, power sources, and the like included in sensor node 200 may be coupled via the generalized bus 230. Bus 230 may include communication and/or power busses.

Figure 2B:
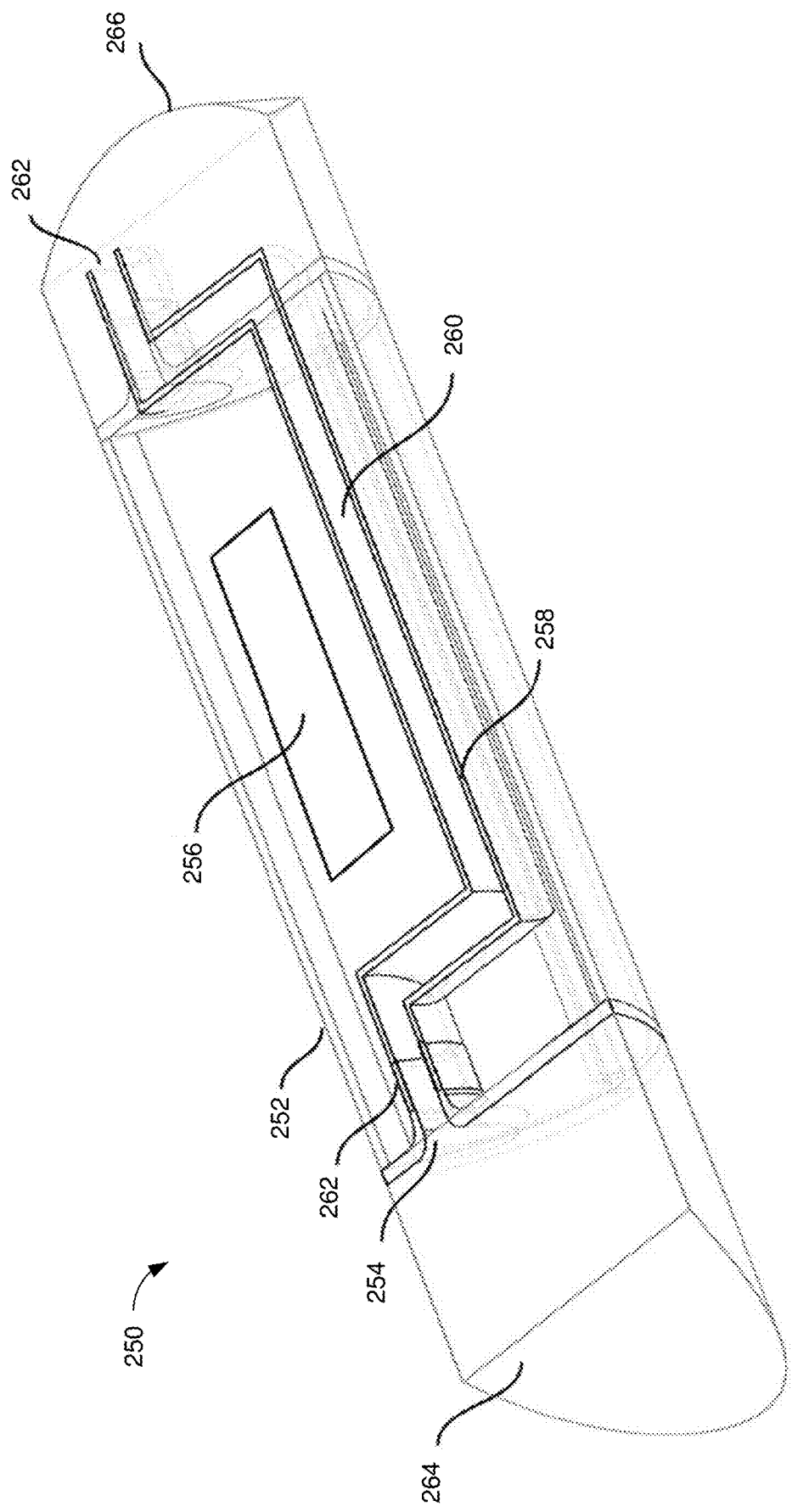
FIG. 2B illustrates another exemplary embodiment of a sensor node that may be employed in the system of FIG. 1.

FIG. 2B illustrates another exemplary embodiment of a sensor node 250 that may be employed in the system 100 of FIG. 1. Sensor node 250 may be employed as a sensor node within a stormwater sensor localized-network (SSLN), such as but not limited to SSLN A 120 and/or SSLN B 130 of FIG. 1. As such, sensor node 250 may include similar features, components, devices, sensors, and the like of sensor node 200 of FIG. 2A. Thus, sensor node 250 may be employed in a stormwater sensor localized-network (SSLN), such as but not limited to SSLN A 120 and/or SSLN B 130 of FIG. 1. Sensor node 250 includes a housing 252 that houses the various components, sensors, devices, and communication/power buses of sensor node 250. Sensor node 250 includes inlet-fluid cover 264 that covers fluid inlet 254. Sensor node 250 also includes fluid-outlet cover 266 that covers fluid outlet 262. Fluid flow channel 258 enables fluid communication between fluid inlet 254 and fluid outlet 262, i.e. fluid 260 may flow between fluid inlet 254 and fluid outlet 262. Fluid-inlet cover 264 and fluid-outlet cover 266 may include one or more screens, mesh, and/or filters that may keep fluid flow channel 258 free of debris and/or sediment that cannot pass through fluid-inlet cover 264 and/or fluid-outlet cover 266.

Fluid 260 within fluid flow channel 258 is exposed to the various sensors included in sensor array 262. At least a portion of the electronic components and/or devices, such as but not limited to power sources, logic devices, data storage devices, global positioning devices, and data transmitter devices may be included and/or integrated with circuit board 256. That is, circuit board 256 may be populated with various electronic devices included with sensor array 250.

Figure 2C:
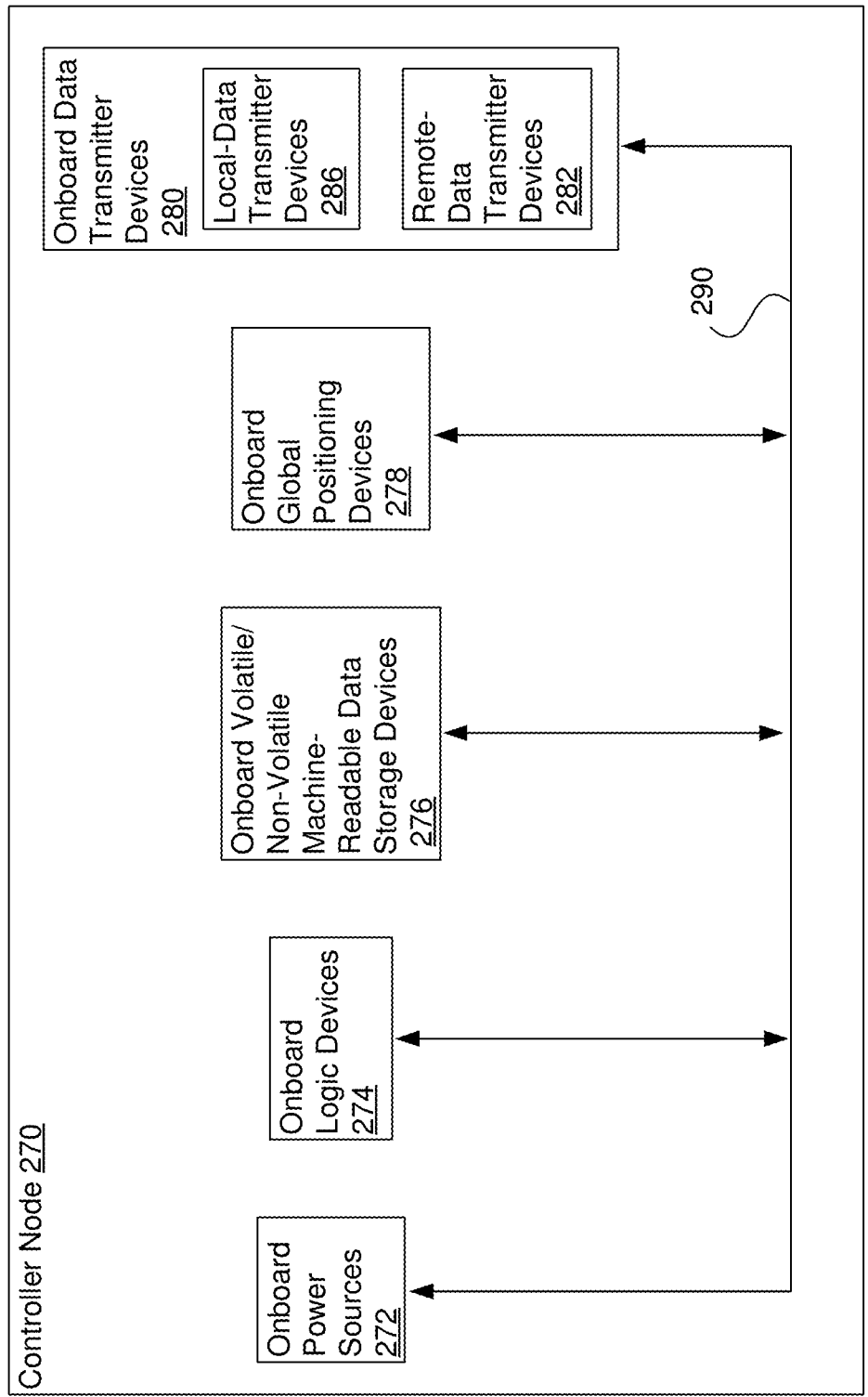
FIG. 2C schematically illustrates an exemplary embodiment of a controller node that may be employed in the system of FIG. 1.

FIG. 2C schematically illustrates an exemplary embodiment of a controller node 270 that may be employed in the system 100 of FIG. 1. Controller node 270 may be employed as a controller node within a stormwater sensor localized-network, such as but not limited to SSLN A 120 and/or SSLN B 130 of FIG. 1. For instance, controller node 270 may be employed as any of controller nodes 122 and/or 132. In some embodiments, controller node 270 may be a data-collection device.

Controller node 270 may include onboard power sources 272, such as but not limited to rechargeable and/or replaceable batteries to provide AC and/or DC power to the various other components, devices, and sensors of sensor node 200. Onboard power sources 272 may include AC ports to provide AC power. Controller node 270 may include one or more onboard logic devices. Such logic devices include, but are not otherwise limited to microprocessors, microcontrollers, central processing units (CPUs), field programmable gate arrays (FPGAs), application specific integrated circuits (ASICs), systems-on-a-chip (SOC), and the like. In some embodiments, the logic devices may perform data transmission routing operations.

Controller node 270 may additionally include various onboard volatile and/or non-volatile machine-readable data storage devices 376 to at least temporally store, buffer, and/or cache data, such as but not limited to storm water. Such data storage devices include, but are not otherwise limited to SRAM devices, (S)DRAM devices, EEPROM devices, FLASH devices, and the like. Controller node 270 may include one or more onboard global positioning devices 278. Such global positioning devices 278 may include global positioning satellite (GPS) receivers to determine the geo-coordinates of a geo-location of controller node 270.

Controller node 270 may also include onboard data transmitter devices 280 to transmit and receive information, such as but not limited to stormwater data. Data transmitter devices 280 may enable data transmission. For instance, onboard transmitter devices 280 includes local-data transmitter devices 246, which enables local-data transmission within a SSLN, and remote-data transmitter devices 282, which enables remote-data transmission to outside the SSLN. For instance, local-data transmitter devices 246 may include radio-frequency (RF) data-transmission devices. In various embodiments, remote-data transmission devices may include various WiFi-enabled devices, Bluetooth enabled devices, Ethernet-enabled devices, or the like, Note that each of these devices, components, sensors, power sources, and the like included in controller node 270 may be coupled via the generalized bus 290. Bus 290 may include communication and/or power busses.

Figure 3A:
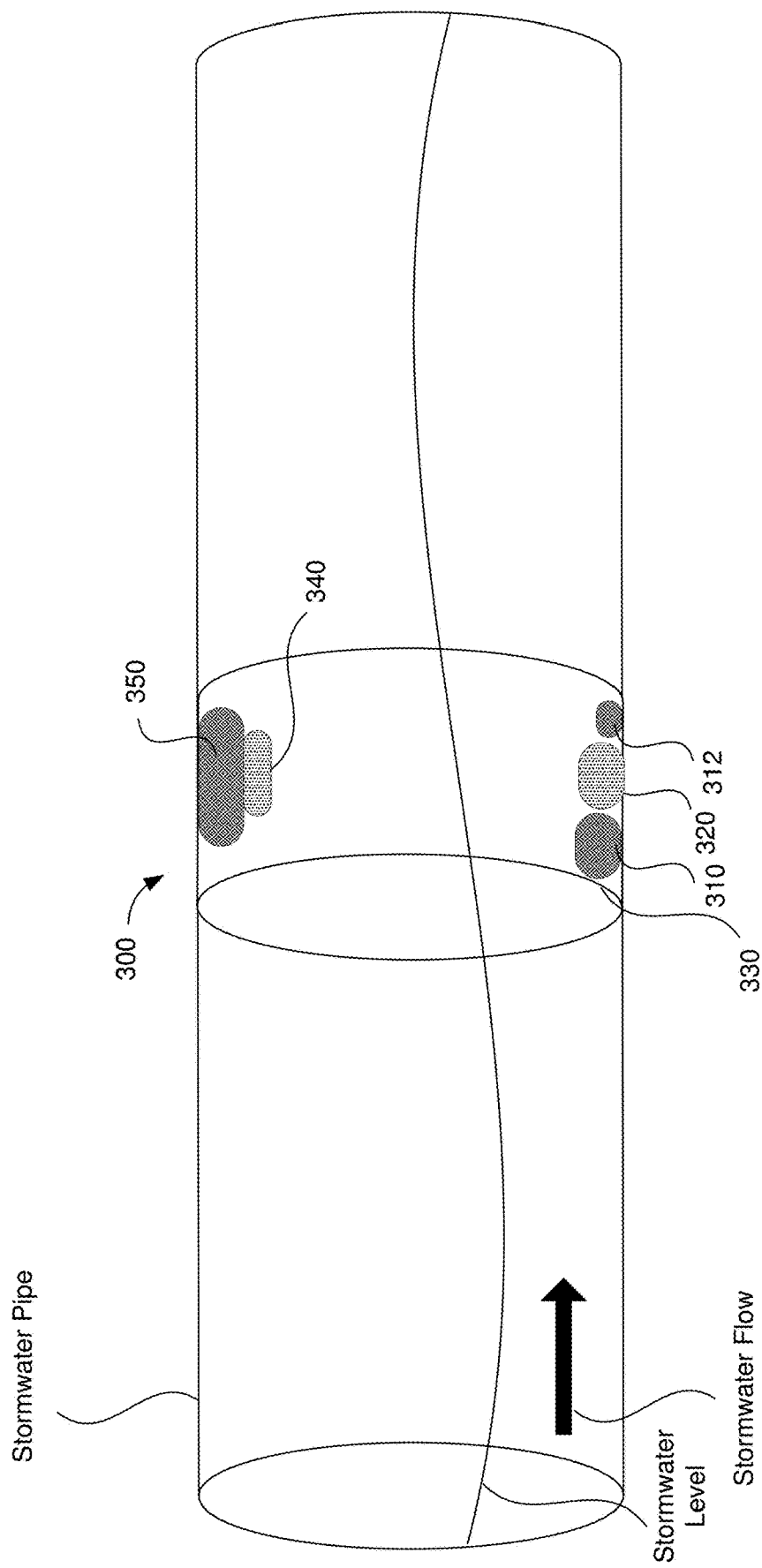
FIGS. 3A-3B illustrate still another exemplary embodiment of a sensor node that may be employed in the system of FIG. 1.
Figure 3B:
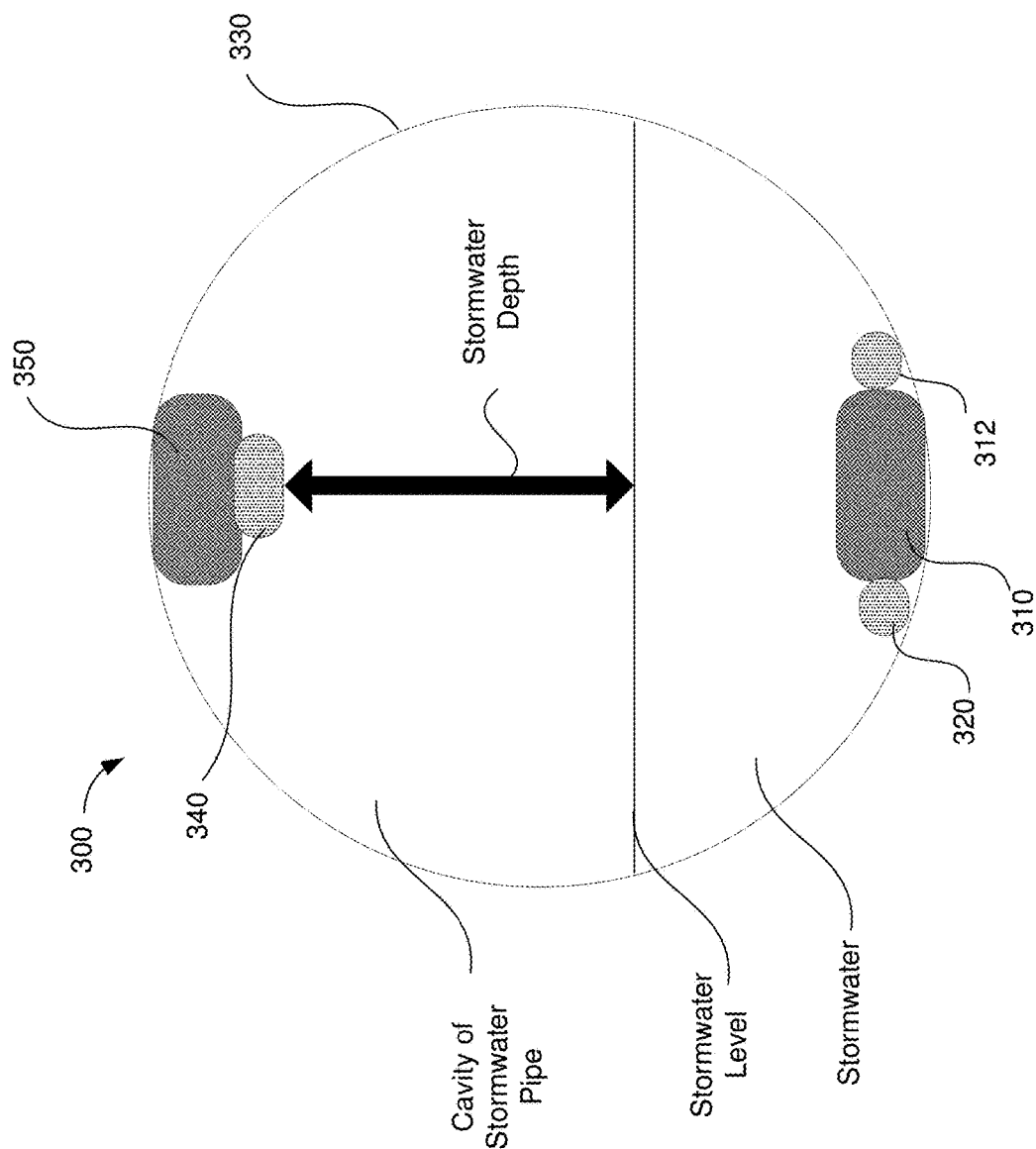

FIGS. 3A-3B illustrate still another exemplary embodiment of a sensor node 300 that may be employed in the system of FIG. 1. FIG. 3A shows an off-axis view of the sensor node 300 within a stormwater pipe, with stormwater flowing through the Sensor node 300 may include a compressions ring 330 that is inserted into the cavity of a stormwater pipe. FIGS. 3A-3B illustrate still another exemplary embodiment of a sensor node that may be employed in the system of FIG. 1. FIG. 3B shows a lateral cross-sectional view of sensor node 300 within the cavity of the stormwater pipe. Compression ring 330 holds the sensor node 300 in place with an outward force exerted on the inner walls of the stormwater pipe Sensor node 300 may include a fluid temperature sensor 310 the acquire stormwater data relating to the temperature of the stormwater. Sensor node 300 may include an ultrasonic Doppler signal sensor 320 to acquire data regarding the velocity of the slowing stormwater. Sensor node 300 may include a pH-level sensor 312 to acquire data regarding the pH-level of the stormwater.

Sensor node 300 may include a ultrasonic depth sensor 340 to acquire storm data regarding the stormwater depth. Housing 350 may house other various electronic components, such as but not limited other sensors, onboard power sources (e.g. rechargeable batteries) onboard logic devices, onboard data storage devices, onboard global positioning devices, onboard data transmitter devices, and the like.

Generalized Processes for a Stormwater Monitoring and Reporting System

Processes 400-700 of FIGS. 4-7 will now be discussed. Briefly, processes 400-700 may be employed to simultaneously and actively monitor stormwater, as well as other fluids, across multiple remote locations, areas, regions, and the like that is consistent with the various embodiments discussed herein. Such processes may be implemented, executed, or otherwise performed via a single and/or a combination of the various embodiments discussed herein. System 100 of FIG. 1 may enable such processes. In various embodiments, computing devices, such as but not limited to user-computing device 102-108 of FIG. 1, or computing device 800 of FIG. 8, are enabled to carry out at least portions of processes 400-700. In some embodiments, a stormwater monitoring application (SMA), such as any of those shown in FIG. 1 may enable at least portions of processes 400-700.

Figure 4:
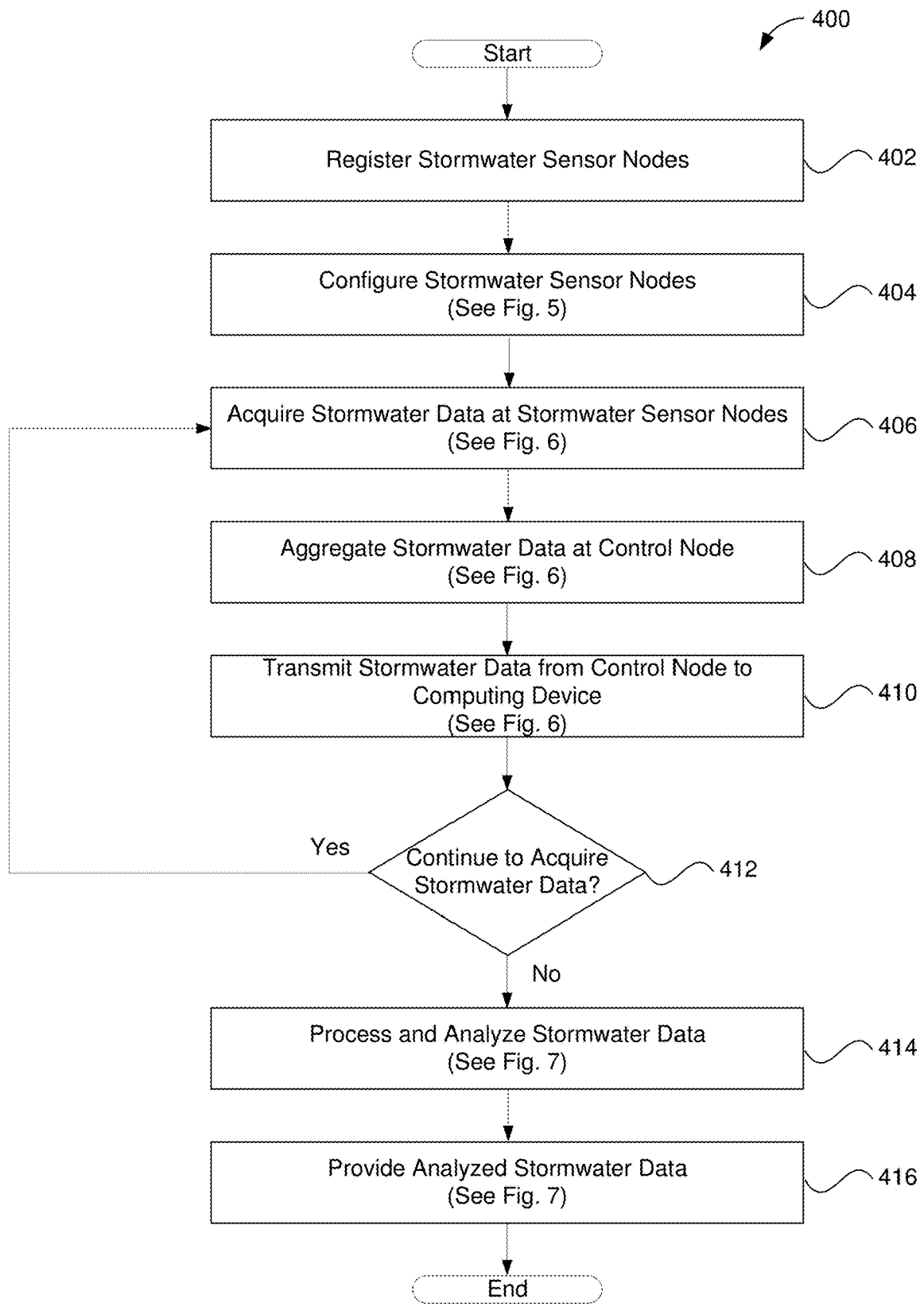
FIG. 4 illustrates one embodiment of a process flow for actively monitoring stormwater and providing stormwater data that is consistent with the various embodiments presented herein.

FIG. 4 illustrates one embodiment of a process flow for actively monitoring stormwater and providing stormwater data that is consistent with the various embodiments presented herein. Process 400 begins, after a start block, at block 402 where a plurality of stormwater sensor nodes are registered. The sensor nodes may be included in a stormwater sensor localized network (SSLN). At noted throughout, the SSLN may be configured in a self-healing mesh network topology. Each of the sensor nodes included in SSLN A 120 of FIG. 1 may be registered at block 402. The sensor nodes of the SSLN may be distributed across at least a portion of a stormwater drainage system.

In various embodiments, the location of each sensor node may be registered at block 402. In some embodiments, a user may employ a user-computing device that is hosting and/or executing a SMA, such as but not limited to SMSA 160, SMCA 180, and/or SSMA 190 of FIG. 1, to provide the locations of the sensor nodes. The locations of each sensor node may include the geo-location of the sensor node in any geographic coordinate system, i.e. the geo-coordinates. In at least one embodiment, the geo-location of at least a portion of the sensor nodes is automatically determined via onboard positioning devices included in the sensor nodes.

The location of each sensor node may be stored. For instance, the sensor node geo-locations may be stored, logged, and/or archived in sensor registration and configuration data 114 of storage device 112 of FIG. 1. The user may employ the SMA to associate and register a unique sensor node identification with the geo-location. In some embodiments, registering and associating the sensor node identification with the geo-location of the sensor node via an interrogation of the sensor node. For instance, a media access control (MAC) address or some other unique identifier of the sensor node may be determined automatically via an interrogation of the sensor node. The geo-location and the associated sensor node identifications may be registered in a database stored in sensor registration and configuration data 114.

At block 404, the registered stormwater sensor nodes may be configured. Various embodiments of configuring stormwater sensor nodes are discussed in conjunction with at least process 500 of FIG. 5. However, briefly here, a user may employ a user-computing device to provide a sensor configuration for each of the sensor nodes. A sensor node configuration may include data-acquisition frequencies and data-transmission frequencies. The sensor configuration may be provided to a controller node of the SSLN. The controller node may provide the corresponding sensor configuration to each of the sensor nodes. In some embodiments, a controller node configuration is also provided to the controller node at block 404.

At block 406, each of the sensor nodes may be employed to acquire stormwater data. At block 408, the stormwater data from each of the sensor nodes may be aggregated at the controller node of the SSLN. Because the controller node aggregates stormwater data from the plurality of nodes, the controller node may be a data-collection device. At block 410, the aggregated stormwater data is periodically provided and/or transmitted to the user-computing device. Various embodiments of acquiring stormwater data, aggregating the stormwater data, and transmitting the stormwater data to the user-computing device are discussed in conjunction with at least process 600 of FIG. 6.

At decision block 412, it is determined whether to continue to acquire stormwater data. If stormwater data acquisition is to be continued, process 400 returns to block 406 to acquire additional stormwater data. Otherwise, process 400 flows to block 414.

At block 414, user-computing device is employed to process and analyze the stormwater data. Various embodiments for processing and analyzing the stormwater data are discussed in conjunction with at least process 700 of FIG. 7. However briefly here, the stormwater data may be normalized and calibrated at the user-computing device. Various stormwater measurements may be determined at block 414. For instance, the Gauckler-Manning coefficient of the stormwater drainage system may be determined. At block 416, the analyzed stormwater data may be provided. Various embodiments of providing the analyzed stormwater data are also discussed in conjunction with FIG. 7. Process 400 may terminate upon completion of 416.

Figure 5:
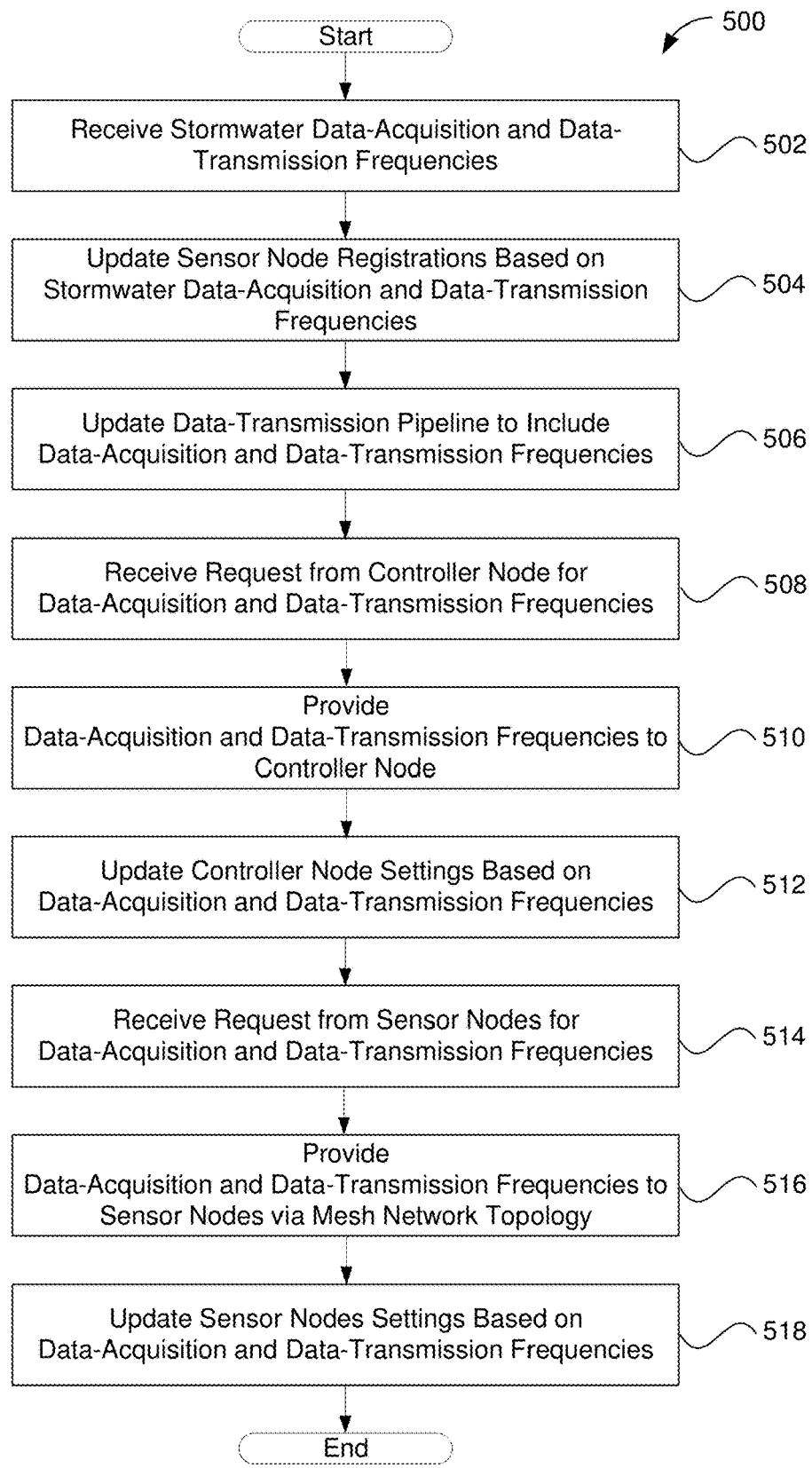
FIG. 5 illustrates one embodiment of a process flow for configuring sensor nodes that is consistent with the various embodiments.

FIG. 5 illustrates one embodiment of a process flow for configuring sensor nodes that is consistent with the various embodiments. Process 500 begins, after a start block, at block 502, where storm data-acquisition frequencies and stormwater data-transmission frequencies are received at the user-computing device. For instance, the user may employ a stormwater monitoring application (SMA), such as but not limited to SMSA 160, SMCA 180, and/or SSMA 190 of FIG. 1, to provide the frequencies. Briefly, the sensor configuration for each sensor node may include a stormwater data-acquisition frequency and a data-transmission frequency. The sensor node may acquire (i.e. sample) stormwater data at the data-acquisition frequency. The sensor node may buffer and transmit the acquired stormwater data to the controller node at the data-transmission frequency of the sensor node configuration.

At block 504, the sensor node registrations are updated based on the stormwater data-acquisition and data-transmission frequencies. That is, the registrations of block 402 of FIG. 4 may be updated to include the various sensor configurations of the sensor nodes. The controller node registration may also be updated at block 402 to include the configuration of the controller node. The sensor and/or controller node updated registrations may be stored at the storage device 112 of FIG. 1

At block 506, a data pipeline may be updated to push, transmit, and/or otherwise provide the sensor configurations (including the data-acquisition and data-transmission frequencies) to the controller node of the SSLN. The pipeline may be updated to also provide the controller node configuration to the controller node. The pipeline may be enabled, managed, or other maintained by the SMA. At block 508, a request for the data-acquisition and data-transmission frequencies may be received. For instance, the controller node of the SSLN may be scheduled to request the sensor configurations for the sensor node from the SMA. Thus, the request received at block 508 may include a request from the controller node (to the SMA) for the sensor configurations. At block 510, the sensor configurations (including the data-acquisition and data-transmission frequencies) are provided to the controller node. At block 510, the controller node configuration may also be provided to the controller node At block 512, the controller node settings may be updated based on the data-acquisition and data-transmission frequencies, as well as other settings, parameters, and the like of the sensor configurations. For instance, the settings of the controller node may be updated so that the controller node expects to receive stormwater data from each of the sensor nodes at the data-transmission frequencies of the stormwater nodes. The controller node may also be set to transmit the stormwater data to the SMA at the same (or separate) data-transmission frequency as the sensor nodes transmit the data to the controller node.

At block 514, a request from each of the sensor nodes may be received. The request from a sensor node may be a request for its sensor configuration, including the data-acquisition and data-transmission frequencies. At block 516, at least the corresponding data-acquisition and data-transmission frequencies are provided to each of the sensor nodes. Other configuration parameters may be provided to the sensor nodes at block 516. The mesh network topology of the SSLN may be employed to provide the sensor configuration to the sensor nodes at block 516.

At block 518, the settings of the sensor nodes are updated based on the sensor configuration. For instance, the settings of a sensor node may update based on the data-acquisition, data-transmission frequencies, or other configurations of the sensor node. That is to say the sensor node may be configured at block 518. Process 500 may terminate upon completion of block 518.

Figure 6:
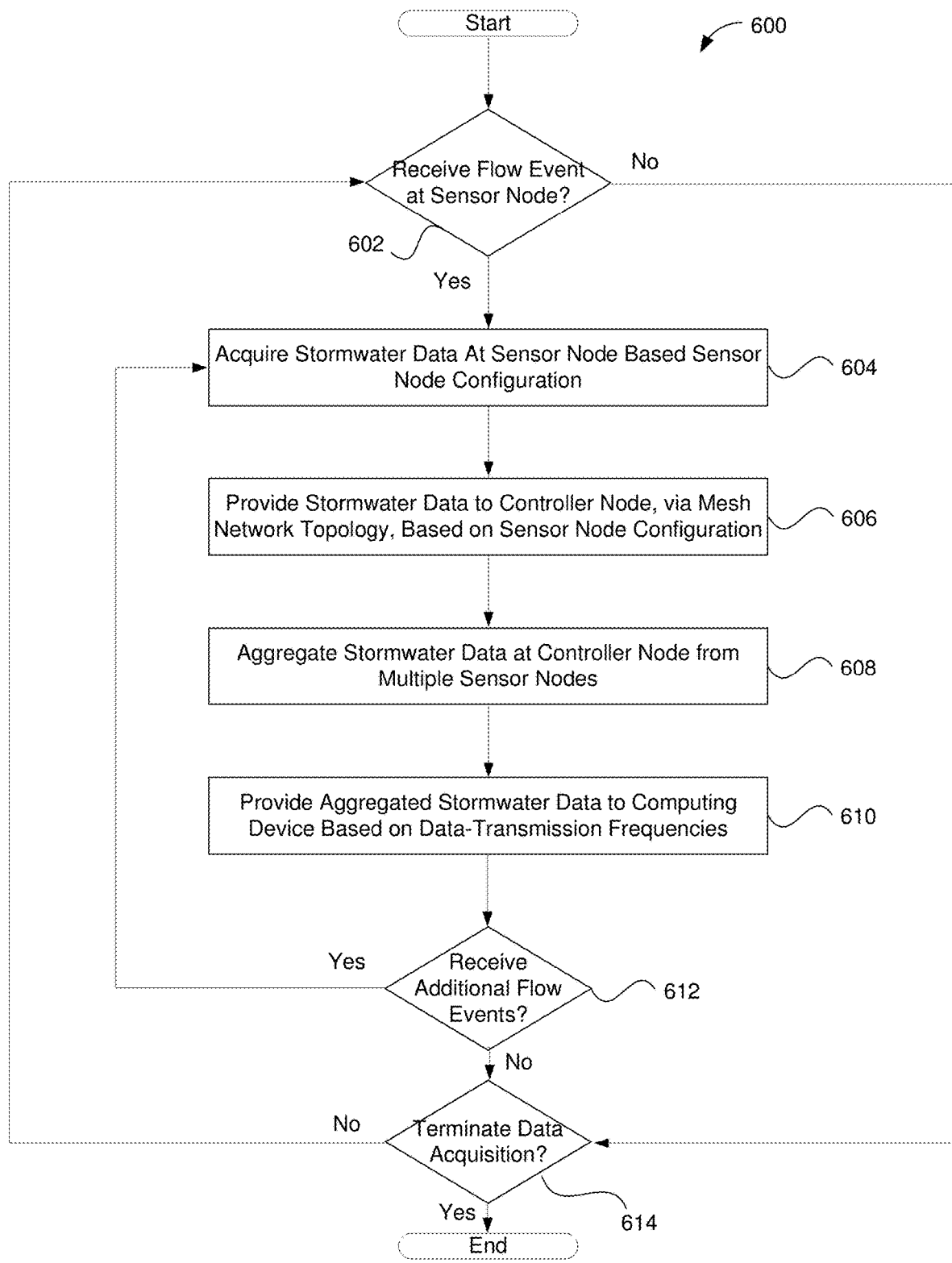
FIG. 6 illustrates one embodiment of a process flow for acquiring and aggregating stormwater data from stormwater sensor nodes that is consistent with the various embodiments.

FIG. 6 illustrates one embodiment of a process flow for acquiring and aggregating stormwater data from stormwater sensor nodes that is consistent with the various embodiments. Process 600 begins, at decision block 602, where it is determined whether a fluid-flow event is received at a sensor node. A fluid flow event may be triggered at a sensor node via the detection of fluid flowing at a rate and/or volume that is greater than a predetermined flow-event threshold.

A fluid flow event may be alternatively triggered via the end of data-acquisition cycle, where the period of the data-acquisition cycle is based on the data-acquisition frequency. For instance, at discussed in conjunction with at least process 500 of FIG. 5, the sensor node configuration may include a data-acquisition frequency. For instance, the data-acquisition frequency may be 1 data-acquisition/hr. Thus, the at decision block 602, a flow event may receive based on the detection of fluid flowing and/or a data-acquisition frequency. In such embodiments, the sensor node may acquire data once an hour, until the flow of a fluid is detected greater than the flow-event threshold. In such an event, the sensor node may acquire stormwater data at greater frequency than the data-acquisition frequency. If a flow event at the sensor node is received, process 600 flows to 604 to acquire stormwater data. Otherwise, process 600 returns to decision block 602 to wait for a flow event.

At block 604, the sensor node is employed to acquire stormwater data. At least a portion of the sensors included in a sensor may acquire stormwater data. For instance, stormwater data may include fluid data relating to any of fluid volume, fluid flow rate, fluid turbidity, fluid pH-level, fluid viscosity, fluid temperature, fluid velocity, fluid depth, and the like. The stormwater data may be acquired based on the sensor node configuration, i.e. once an hour or any other data-acquisition frequency.

At block 606, the stormwater data is provided to the controller node, via the network topology of the SSLN. The stormwater data may be provided to the controller node at a rate based on the data-transmission frequency, i.e. the sensor nodes may transmit or otherwise prove the acquired stormwater data at a rate that is consistent with the data-transmission frequency. Each sensor may provide its acquired stormwater data to the controller node via a plurality of stormwater data packets. The data packets may include various metadata, such as but not limited to the sensor node identification. At block 608, the stormwater data is aggregated at the controller node, i.e. the stormwater data packets for each of the sensor nodes may be aggregated at the controller node. Because the controller node aggregates stormwater data from the plurality of nodes, the controller node may be a data-collection device. The stormwater data may be aggregated from each of the sensor nodes of the SSLN.

At block 610, the aggregated stormwater data is provided to the user-computing device based on the data-transmission frequency of the controller node. Thus, at block 610, the stormwater data packets may be provided to the user-computing device. A communication network, such as but not limited to communication network 110 of FIG. 1 may be employed to provide the user-computing device the stormwater data. In various embodiments, the stormwater data is provided to a SMA that is hosted and/or executed by the user-computing device. Note that the data-transmission frequency of the controller node may be separate than the data-transmission frequency of the sensor nodes.

At decision block 612, it is determined whether an additional flow event is received. If an additional flow event (either triggered by the flow of fluid and/or the data-acquisition frequency of the sensor nodes) is received at a sensor node, process 600 returns to block 604 to acquire additional stormwater data. Otherwise, process 600 flows to decision block 614. At decision block 614, it is determined whether to terminate stormwater data acquisition. If data acquisition is not to be terminated, process 600 returns to decision block 602 to wait for another flow event. Otherwise, process 600 may be terminated.

Figure 7:
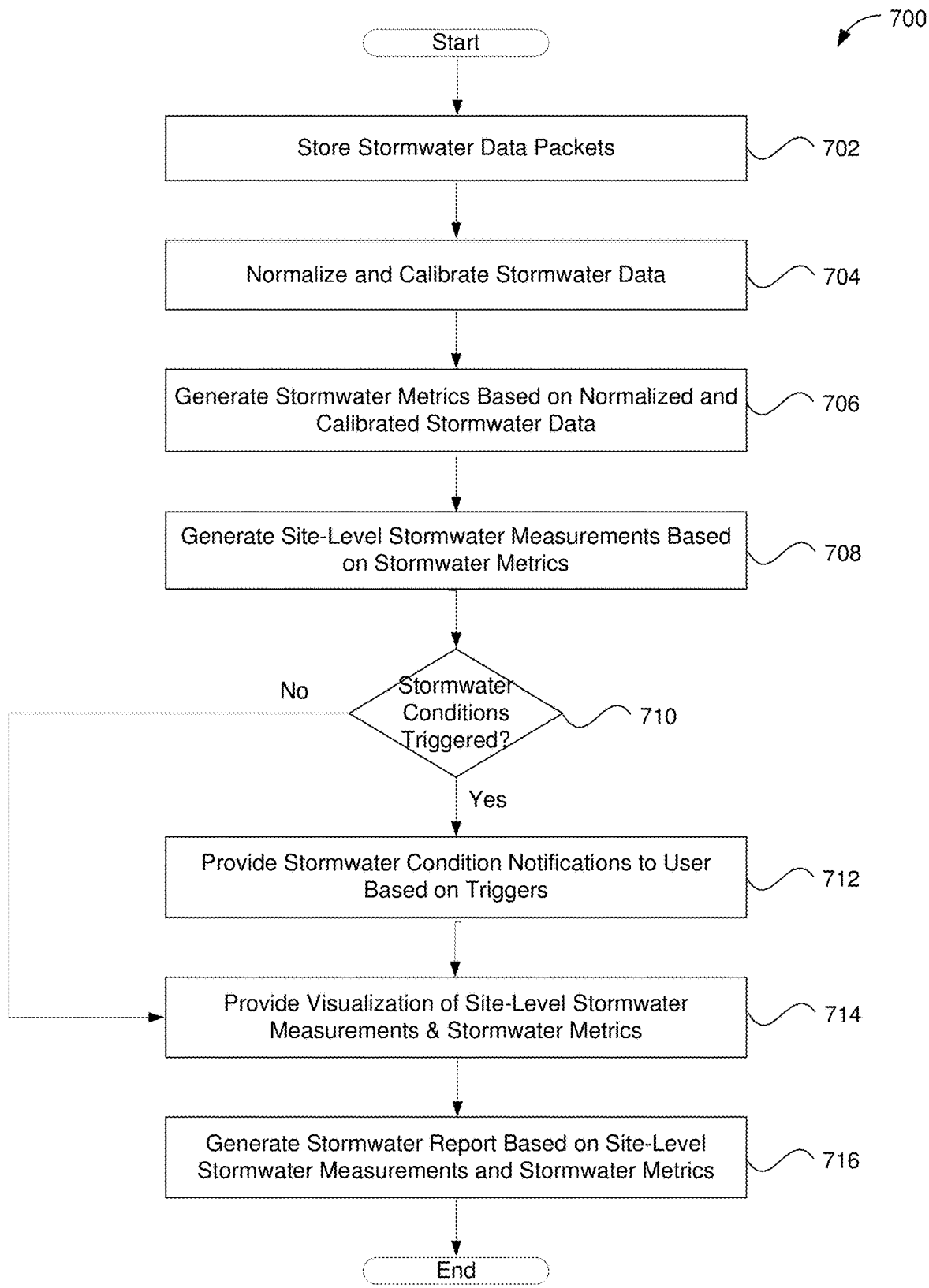
FIG. 7 illustrates one embodiment of a process flow for processing, analyzing, and reporting of stormwater data that is consistent with the various embodiments.
Figure 8:
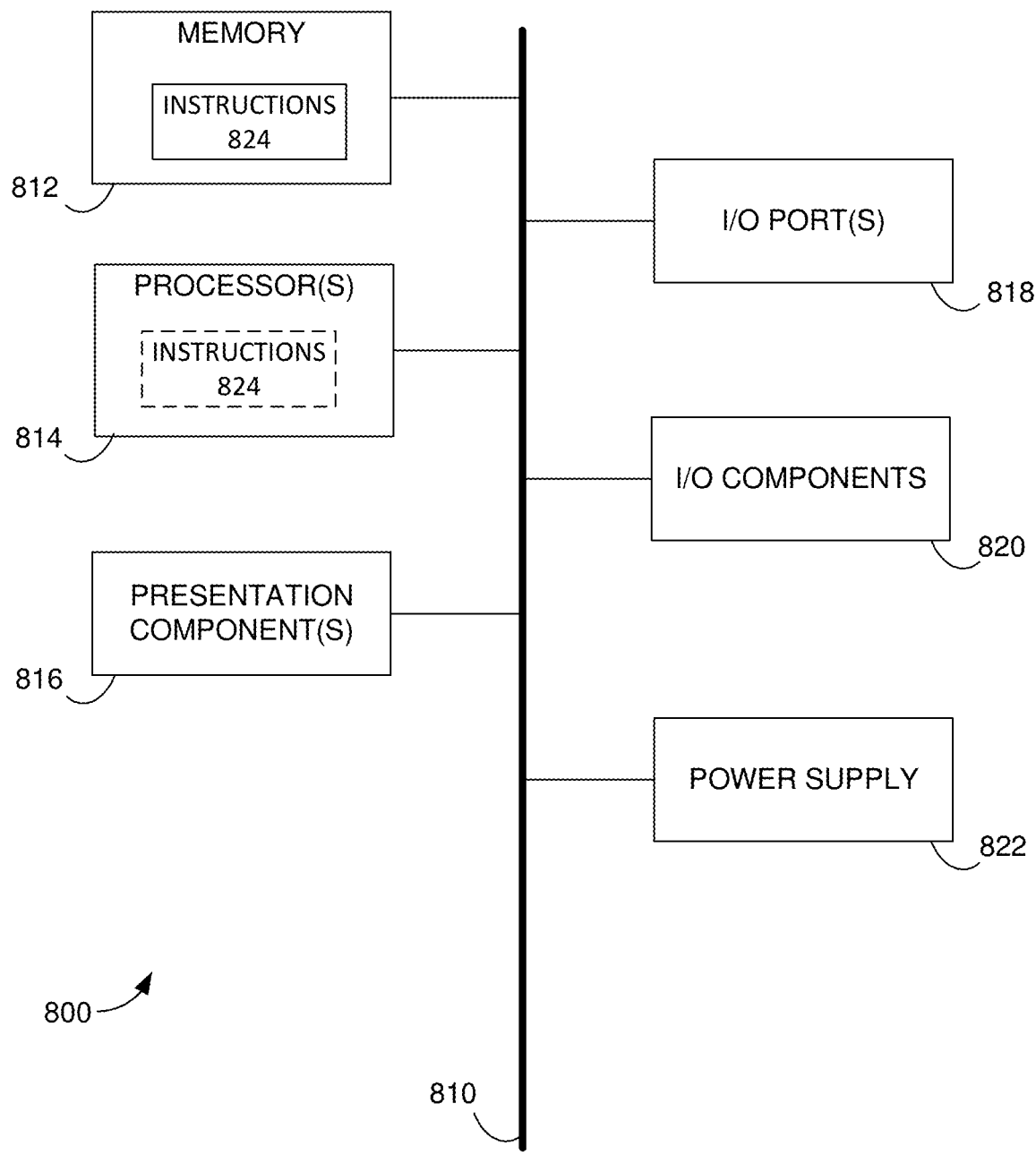
FIG. 8 is a block diagram of an example computing device in which embodiments of the present disclosure may be employed.

FIG. 7 illustrates one embodiment of a process flow for processing, analyzing, and reporting of stormwater data that is consistent with the various embodiments. Process 700 starts, after a start block, at block 702 where storm water data packets are stored. For instance storm water data packets may be received from the controller node. The storm water data packets may be stored in a storage device, such as but not limited to storage device 112 of FIG. 1. Accordingly, the storm water data may be logged and/or archived at block 702.

At block 704, the storm water data is normalized. The storm water data may also be calibrated at block 704. At block 706 one or more storm water metrics may be generated based on the normalized calibrated stormwater data. For instance various storm water metrics may be derived from the calibrated stormwater data. The SMA may determine a Gauckler-Manning coefficient for the stormwater drainage system based on the stormwater metrics.

At block 410, site-level measurements may be generated based on the stormwater metrics. For each SSLN, the SMA may combine the corresponding stormwater metrics to generate one or more site-level stormwater measurements. A site-level stormwater measurement may correspond to stormwater measurements for the sit covered by the SSLN. For instance, the stormwater metrics may be combined to generate a site-level average flow rate, average flow volume, or the like.

At decision block 710, it is determined whether to a stormwater condition is triggered based on the site-level measurements. If a stormwater condition is triggered, process 700 flows to block 712. Otherwise process 700 may flows to block 714. At block 712, one or more stormwater condition notifications may be provided to a user of the SMA based on the triggers. For instance, is a stormwater flow velocity of the stormwater exceeds a flow-velocity threshold, based on the stormwater data, the SMA may provide a notification to a user.

At block 714, visualizations of the site-level stormwater measurements may be provided to the user of the SMA. For instance, a displace device of the user-computing device may be employed to display various plots, charts, graphs, and the like, based on the stormwater metrics. At block 716, one or more stormwater reports may be generated based on the site-level stormwater measurements and/or the stormwater metrics. The stormwater reports may be stored in the data storage device of FIG. 1. Process 700 may terminate after execution of block 716.

Illustrative Computing Device

Having described embodiments of the present invention, an example operating environment in which embodiments of the present invention may be implemented is described below in order to provide a general context for various aspects of the present invention. Referring to FIG. 8, an illustrative operating environment for implementing embodiments of the present invention is shown and designated generally as computing device 800. Computing device 800 is but one example of a suitable computing environment and is not intended to suggest any limitation as to the scope of use or functionality of the invention. Neither should the computing device 800 be interpreted as having any dependency or requirement relating to any one or combination of components illustrated.

Embodiments of the invention may be described in the general context of computer code or machine-useable instructions, including computer-executable instructions such as program modules, being executed by a computer or other machine, such as a smartphone or other handheld device. Generally, program modules, or engines, including routines, programs, objects, components, data structures, etc., refer to code that perform particular tasks or implement particular abstract data types. Embodiments of the invention may be practiced in a variety of system configurations, including hand-held devices, consumer electronics, general-purpose computers, more specialized computing devices, etc. Embodiments of the invention may also be practiced in distributed computing environments where tasks are performed by remote-processing devices that are linked through a communications network.

With reference to FIG. 8, computing device 800 includes a bus 810 that directly or indirectly couples the following devices: memory 812, one or more processors 814, one or more presentation components 816, input/output ports 818, input/output components 820, and an illustrative power supply 822. Bus 810 represents what may be one or more busses (such as an address bus, data bus, or combination thereof). Although the various blocks of FIG. 8 are shown with clearly delineated lines for the sake of clarity, in reality, such delineations are not so clear and these lines may overlap. For example, one may consider a presentation component such as a display device to be an I/O component, as well. Also, processors generally have memory in the form of cache. We recognize that such is the nature of the art, and reiterate that the diagram of FIG. 8 is merely illustrative of an example computing device that can be used in connection with one or more embodiments of the present disclosure. Distinction is not made between such categories as "workstation," "server," "laptop," "hand-held device," etc., as all are contemplated within the scope of FIG. 8 and reference to "computing device."

Computing device 800 typically includes a variety of computer-readable media. Computer-readable media can be any available media that can be accessed by computing device 800 and includes both volatile and nonvolatile media, removable and non-removable media. By way of example, and not limitation, computer-readable media may comprise computer storage media and communication media.

Computer storage media include volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 800. Computer storage media excludes signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 812 includes computer storage media in the form of volatile and/or nonvolatile memory. Memory 812 may be non-transitory memory. As depicted, memory 812 includes instructions 824. Instructions 824, when executed by processor(s) 814 are configured to cause the computing device to perform any of the operations described herein, in reference to the above discussed figures, or to implement any program modules described herein. The memory may be removable, non-removable, or a combination thereof. Illustrative hardware devices include solid-state memory, hard drives, optical-disc drives, etc. Computing device 800 includes one or more processors that read data from various entities such as memory 812 or I/O components 820. Presentation component(s) 816 present data indications to a user or other device. Illustrative presentation components include a display device, speaker, printing component, vibrating component, etc.

I/O ports 818 allow computing device 800 to be logically coupled to other devices including I/O components 820, some of which may be built in. Illustrative components include a microphone, joystick, game pad, satellite dish, scanner, printer, wireless device, etc.

Embodiments presented herein have been described in relation to particular embodiments which are intended in all respects to be illustrative rather than restrictive. Alternative embodiments will become apparent to those of ordinary skill in the art to which the present disclosure pertains without departing from its scope.

From the foregoing, it will be seen that this disclosure in one well adapted to attain all the ends and objects hereinabove set forth together with other advantages which are obvious and which are inherent to the structure.

It will be understood that certain features and sub-combinations are of utility and may be employed without reference to other features or sub-combinations. This is contemplated by and is within the scope of the claims.

In the preceding detailed description, reference is made to the accompanying drawings which form a part hereof wherein like numerals designate like parts throughout, and in which is shown, by way of illustration, embodiments that may be practiced. It is to be understood that other embodiments may be utilized and structural or logical changes may be made without departing from the scope of the present disclosure. Therefore, the preceding detailed description is not to be taken in a limiting sense, and the scope of embodiments is defined by the appended claims and their equivalents.

Various aspects of the illustrative embodiments have been described using terms commonly employed by those skilled in the art to convey the substance of their work to others skilled in the art. However, it will be apparent to those skilled in the art that alternate embodiments may be practiced with only some of the described aspects. For purposes of explanation, specific numbers, materials, and configurations are set forth in order to provide a thorough understanding of the illustrative embodiments. However, it will be apparent to one skilled in the art that alternate embodiments may be practiced without the specific details. In other instances, well-known features have been omitted or simplified in order not to obscure the illustrative embodiments.

Various operations have been described as multiple discrete operations, in turn, in a manner that is most helpful in understanding the illustrative embodiments; however, the order of description should not be construed as to imply that these operations are necessarily order dependent. In particular, these operations need not be performed in the order of presentation. Further, descriptions of operations as separate operations should not be construed as requiring that the operations be necessarily performed independently and/or by separate entities. Descriptions of entities and/or modules as separate modules should likewise not be construed as requiring that the modules be separate and/or perform separate operations. In various embodiments, illustrated and/or described operations, entities, data, and/or modules may be merged, broken into further sub-parts, and/or omitted.

The phrase "in one embodiment" or "in an embodiment" is used repeatedly. The phrase generally does not refer to the same embodiment; however, it may. The terms "comprising," "having," and "including" are synonymous, unless the context dictates otherwise. The phrase "A/B" means "A or B." The phrase "A and/or B" means "(A), (B), or (A and B)." The phrase "at least one of A, B and C" means "(A), (B), (C), (A and B), (A and C), (B and C) or (A, B and C)."

What is claimed is:

1. A computer-readable non-transitory storage medium having instructions stored thereon for monitoring fluid, which, when executed by a processor device cause the processor device to perform actions comprising:

providing, by a data-collection device, a portion of a configuration to each of a plurality of fluid sensor devices, wherein the configuration includes at least a data-acquisition frequency and a data-transmission frequency, the portion of the configuration at least includes the data-acquisition frequency;

in response to receiving the portion of the configuration from the data-collection device, updating settings of the plurality of fluid sensor devices such that each of the plurality of fluid sensor devices is configured to acquire fluid data based on the received data-acquisition frequency;

acquiring, by each of the plurality of fluid sensor devices, the fluid data based on the updated settings, wherein the settings are updated based on at least the received data-acquisition frequency;

aggregating, by the data-collection device, the fluid data acquired from each of the plurality of fluid sensor devices; and periodically providing, by the data-collection device, the aggregated fluid data to a user-computing device based on the data-transmission frequency.

* * * * *